United States Patent [19]

Seebach

[11] 4,117,132
[45] Sep. 26, 1978

[54] PROCESS FOR THE PRODUCTION OF STABILIZED PURE THEOPHYLLINE IN NEUTRAL, AQUEOUS SOLUTION

[75] Inventor: Adolf Seebach, Zurich, Switzerland

[73] Assignee: Dr. Adolf Seebach AG, Zurich, Switzerland

[21] Appl. No.: 740,672

[22] Filed: Nov. 10, 1976

[30] Foreign Application Priority Data

Apr. 2, 1976 [CH] Switzerland .......................... 4152/76

[51] Int. Cl.$^2$ ............................................. A61K 31/52
[52] U.S. Cl. .................................................. 424/253
[58] Field of Search ......................................... 424/253

[56] References Cited

U.S. PATENT DOCUMENTS

| 3,823,229 | 7/1974 | Jederstrom | 424/253 |
| 3,928,609 | 12/1975 | Behrakis | 424/253 |

FOREIGN PATENT DOCUMENTS 620,908  7/1962  Belgium.

OTHER PUBLICATIONS

Maulding et al., Chem. Abst., vol. 74 (1971), p. 80440j.
Maulding et al., J. of Pharm. Sci., vol. 60, No. 2, Feb. 1971, pp. 309–311.

*Primary Examiner*—Sam Rosen
*Attorney, Agent, or Firm*—Cushman, Darby & Cushman

[57] ABSTRACT

A pure, stable, neutral, aqueous solution of theophylline is obtained by adding pure theophylline to a 7-hydroxypropyl derivative of theophylline.

19 Claims, No Drawings

PROCESS FOR THE PRODUCTION OF STABILIZED PURE THEOPHYLLINE IN NEUTRAL, AQUEOUS SOLUTION

BACKGROUND OF THE INVENTION

The object of the present invention is the development of a process which provides a stable, solution of theophylline in pure water without the introduction of foreign solubilizers and which has good solubility under neutral conditions. The invention also includes the novel compositions prepared.

The classical solution to this problem at present is the process for the production of aminophyllines. These compounds are formed by dissolving pure theophylline in strongly alkaline, aqueous solution of aliphatic amines. The most important way of carrying out this process is that for the production of the aminophylline Pharmacopeia V (see also, the United States Pharmacopeia XVIII, pages 33-34). Thereby, pure theophylline is dissolved in an aqueous solution containing 20 parts by weight of ethylene diamine (pH about 10). However, all of these solutions are chemically unstable because of their high dependency on pH. In such solutions, even the carbonic acid from the air can cause a precipitation of the pure theophylline. This is also true in the stomach due to the free hydrochloric acid. Besides, the ethylene diamine irritates the skin, especially the mucous membrane, which can even lead to dermatitis. With alkaline solutions, besides it is very problematical that mixtures are formed with other medicines because of the precipitation of the dissolved materials. Likewise, because of the strongly alkaline solution, the blood vessels are irritated in the injection of the solution.

All of these defects are eliminated by the use of the process of the present invention as well as by the use of the products produced thereby.

This invention therefore signifies a true advance because the thus obtained aqueous solution is not only chemically stable, but is also practically pH insensitive.

SUMMARY OF THE INVENTION

The present invention comprises a process for the production of a stable, neutral aqueous pure solution of theophylline by dissolving a 7-hydroxypropyl derivative of theophylline in water and adding pure theophylline to this neutral solution.

Besides, the process of the invention also includes the products obtained and their special uses.

As 7-hydroxypropyl theophyllines there can be used for example proxyphylline [7-(2-hydroxypropyl)-theophylline] or diprophylline [7-(2,3-dihydroxypropyl) theophylline] or mixtures thereof in any proportion.

According to the invention, therefore, the theophylline is brought into combination with a 7-hydroxypropyl derivative of theophylline in non-dissociated form in an aqueous medium at a pH of about 7.2.

An aqueous neutral solution may have a content of theophylline which lies within 22.5 to 27.5 weight % and the content of the 7-hydroxypropyl theophyllines lies within 72.5 and 77.5 weight %-both indications related to the total amount of the theophyllines present.

The aqueous solution can be dried and yields a solid composition with corresponding contents. For instance the dry composition may contain 22.5 to 27.5 weight % of theophylline, from 35 to 40 weight % of 7-(2-hydroxypropyl)theophylline and from 35 to 40 weight % of 7-(2,3-dihydroxypropyl)theophylline. This composition can be used in dragées, retard dragées with or without pure theophylline.

The freedom from irritation and the good resorbability of the product as a medicament are assured.

While pure theophylline only is soluble in water to an extent of 0.5 weight %, the solubility of this material in the process of the invention increased to 2 weight % at a total concentration of solids of 8 weight %. (In such a composition, the ratio of 7-hydroxypropyl theophylline to theophylline is 3:1 by weight). Additionally, the product in solution with a total 8 weight % solids concentration show a high powered therapeutic activity based on the pure theophylline.

The process is distinguished by great simplicity. In medicine, the product is primarily used as a bronchospasmolytic as well as in heart and circulatory disturbances.

Unless otherwise indicated, all parts and percentages are by weight.

The composition can comprise, consist essentially of or consist of the materials set forth.

DESCRIPTION OF THE PREFERRED EMBODIMENTS

EXAMPLE 1

15.0 parts by weight of proxyphylline and 15.0 parts by weight of diprophylline were dissolved in 500 parts by weight of distilled water with slight heating (pH = about 7.2). Then, slowly with continuous stirring, there were added 10 parts by weight of pure, anhydrous theophylline as a very fine powder. The clear solution was filtered and sterilized. There were dissolved in this solution 2 weight % of theophylline as a pure, stable, neutral aqueous composition.

A portion of the solution obtained was evaporated to dryness. The residue obtained likewise can be used in solid form as a medicament.

EXAMPLE 2

30 parts by weight of proxyphylline were dissolved in 500 parts of distilled water with slight heating (pH about 7.2). With continuous stirring, there were slowly added 10 parts by weight of pure anhydrous theophylline as a very fine powder. The clear solution was filtered and sterilized. It contained 2 weight % of pure theophylline as a stable, neutral aqueous solution.

Again, a portion of the solution obtained was subsequently evaporated to dryness. The residue obtained likewise can be used as a solid material as a medicament.

The solution can be used, for example, in the form of a microclysma. The solid can be dispersed as a delay dragee alone or simultaneously with pure solid theophylline in delay form.

EXAMPLE 3

Aqueous solution according to the invention for use in microclysmas were prepared. They contained about 2 weight % of pure theophylline and about 3 weight % of proxyphylline and about 3 weight % of diprophylline, ~2 weight % of pure theophylline and about 6 weight % of proxyphylline or about 2 weight % of pure theophylline and about 6 weight % of diprophylline. To these aqueous solutions were added about 1 weight % of methocell, at least one surfactant and at least one preservation agent.

What is claimed is:

1. A process of producing a pure, stable neutral aqueous solution of theophylline at a pH between 7 and 7.4 consisting essentially of adding pure theophylline to a neutral solution of a 7-hydroxypropyl theophylline selected from the group consisting of (a) 7-(2,3-dihydroxypropyl) theophylline and (b) a mixture of 7-(2,3-dihydroxypropyl) theophylline with 7-(2-hydroxypropyl) theophylline, the 7-hydroxypropyl theophylline being present in an amount sufficient to solubilize the theophylline.

2. A process according to claim 1 including the further step of evaporating the solution to dryness.

3. A process according to claim 1 wherein the 7-hydroxypropyl theophylline is 7-(2,3-dihydroxypropyl) theophylline.

4. A process according to claim 3 including the further step of evaporating the solution to dryness.

5. An aqueous neutral solution consisting essentially of water, theophylline, and a 7-hydroxypropyl theophylline selected from the group consisting of (a) 7-(2,3-dihydroxypropyl) theophylline and (b) a mixture of 7-(2,3-dihydroxypropyl) theophylline with 7-(2-hydroxypropyl) theophylline, wherein the content of theophylline lies within 22.5 to 27.5 weight % and contents of the 7-hydroxypropyl theophyllines lie within 72.5 and 77.5 weight % - both indications related to the total amount of present theophyllines.

6. An aqueous solution according to claim 5 containing the theophylline in an amount above 0.5 weight % of the solution, the 7-hydroxypropyl theophylline being present in an amount sufficient to increase the solubility of the theophylline above 0.5 weight %.

7. An aqueous solution according to claim 6 containing 2 weight % theophylline, the amount of 7-hydroxypropyl theophylline being sufficient to increase the solubility of theophylline up to 2 weight %.

8. An aqueous solution according to claim 5 in the form of a microclysma.

9. An aqueous solution according to claim 5 wherein the 7-hydroxypropyl theophylline is 7-(2,3-dihydroxypropyl) theophylline.

10. An aqueous solution according to claim 9 containing the theophylline in an amount above 0.5 weight % of the solution, the 7-(2,3-dihydroxypropyl) theophylline being present in an amount sufficient to increase the solubility of the theophylline above 0.5 weight %.

11. The pure dry solid composition prepared by drying the composition of claim 9.

12. The pure, dry solid composition prepared by drying the composition of claim 5 and containing from 22.5 to 27.5 weight % of theophylline, from 35 to 40 weight % of 7-(2-hydroxypropyl)theophylline and from 35 to 40 weight % of 7-(2,3-dihydroxypropyl)theophylline.

13. A pure, neutral, dry solid composition consisting essentially of a 7-hydroxypropyl theophylline selected from the group consisting of (a) 7-(2,3-dihydroxypropyl) theophylline and (b) a mixture of 7-(2,3-dihydroxypropyl) theophylline with 7-(2-hydroxypropyl) theophylline; and theophylline.

14. A composition according to claim 13 wherein the 7-hydroxypropyl theophylline is present in an amount sufficient to increase the solubility of theophylline in water to above 0.5 weight %.

15. A composition according to claim 14 containing 3 parts of the 7-hydroxypropyl theophylline for each part of theophylline.

16. A composition according to claim 13 in the form of a retard dragee.

17. A process of dispensing theophylline comprising simultaneously administering the delay dragee of claim 16 along with pure solid theophylline in delay form.

18. A composition according to claim 13 wherein the 7-hydroxypropyl theophylline is 7-(2,3-dihydroxypropyl) theophylline.

19. A composition according to claim 18 containing 3 parts of the 7-(2,3-dihydroxypropyl) theophylline for each part of theophylline.

* * * * *

Dedication 4,117,132.—Adolf Seebach, Zurich, Switzerland. PROCESS FOR THE PRODUCTION OF STABILIZED PURE THEOPHYLLINE IN NEUTRAL, AQUEOUS SOLUTION. Patent dated Sept. 26, 1978. Dedication filed Feb. 24, 1981, by the assignee, *Dr. Adolf Seebach, A. G.*

Hereby dedicates to the Public the remaining term of said patent.
[*Official Gazette May 19, 1981.*]